United States Patent [19]

Bradford et al.

[11] Patent Number: Plant 5,662

[45] Date of Patent: Feb. 18, 1986

[54] PLUM TREE (JUNE BEAUT)

[76] Inventors: Norman G. Bradford; Lowell G. Bradford, both of 11875 E. Savana Rd., Le Grand, Calif. 95333

[21] Appl. No.: 622,087

[22] Filed: Jun. 18, 1984

[51] Int. Cl.[4] ..... A01H 5/03

[52] U.S. Cl. ..... Plt./38

[58] Field of Search ..... Plt./38

*Primary Examiner*—Robert E. Bagwill

[57] ABSTRACT

The present invention relates to a plum tree and more particularly to a new and distinct variety broadly characterized by a large, vigorous, upright tree, hardy, regular bearing and very productive, which requires a pollinator. The clingstone fruit is oblate in form, has a dark maroon skin color with yellow specks, greenish-yellow flesh, and a firm and crisp texture. The fruit generally achieves picking ripeness about three to five days after the El Dorado (believed to be patented) but the fruit is larger in size and has a picking time which extends approximately ten days, under the ecological conditions described. The fruit is of good eating and shipping quality.

1 Drawing Figure

BACKGROUND OF VARIETY

The instant plum tree was discovered by us in our orchard at Bradford Farms in Merced County (San Joaquin Valley), Calif., as an open pollinated El Dorado seedling which was selected by us from other such seedlings because of evidencing desirable characteristics for commercial production. The instant variety most nearly resembles the El Dorado plum, an old, well known plum variety believed to have been developed by Luther Burbank. It may be patented, but if so, the patent number is not known to us. The fruit is larger than the El Dorado plum and much darker in color at picking time, and the tree is more vigorous and blooms about five days later. The variety is self-sterile and must be cross-pollinated by another variety.

Subsequent to origination and selection by us of the present variety of plum tree, we asexually reproduced it by budding and grafting, and such reproduction of plant and fruit characteristics were true to the original plant in all respects.

DRAWINGS

The accompanying photograph includes views of whole fruits, showing the characteristics of form and skin color, a characteristic fruit divided on its suture plane showing the flesh color and stone cavity of a clingstone, and a characteristic stone.

POMOLOGICAL CHARACTERISTICS

Referring now more specifically to the pomological characteristics of this new and distinct variety of plum tree, the following has been observed by me under the ecological conditions prevailing near Le Grand, Merced County (San Joaquin Valley), Calif., and was developed at the state of commercial ripeness in the 1983 growing season. All color plate identifications are by reference to Dictionary of Color 1950 (2nd ed) by Maerz and Paul.

TREE

General: Hardy, vigorous, regular bearing and very productive (but requiring a pollinator).

Form: Dense, vase formed, upright.

Size: Large.

Trunk: Of medium size, medium smooth, with brown bark and some small tan lenticles ¼" in length.

Branches: Slender, shaggy; brown color streaks with dark brown, resembling Castor (16 A-8), over tan, resembling Log Cabin (15 A-5). A medium amount of small orange-tan lenticles.

Leaves:

*Size.*—Length, 4½"; width, 2"; medium size.

*Form.*—Eliptical.

*Base.*—Mostly acute.

*Apex.*—Acuminate.

*Margin.*—Crenate.

*Venation.*—Pinnately net veined.

*Thickness.*—Medium.

*Surface.*—Slightly rugose.

*Color.*—Dorsal side, dark green (24 E-1); ventral side green (24 L-1).

*Petiole.*—Medium; average length, ½", average width, 1/6"; medium thickness. Light green with some red on dorsal side, light green on ventral side.

*Glands.*—Averaging two in number, small, globose glands oppositely disposed at base of leaf.

*Stipules.*—A few stipules, averaging ¼" in length.

Flowers:

*Buds.*—Hardy, medium size and length; plump, obtuse form. Free and glabroud.

*Blossoms.*—Blooms at medium season, three days after the Santa Rosa variety (used as a pollinator) and about five days after the El Dorado; medium size; white.

FRUIT

Maturity when described: Hard ripe, July 11, 1983.

*Size.*—Uniformly medium; 1¾" in diameter, 2" in suture plane. Larger than El Dorado.

*Form.*—Uniformly symmetrical; oblate, slightly compressed axially. Slightly oblate in the longitudinal section, globose transversely through diameter.

*Suture.*—Ventral and dorsal surfaces rounded; slightly lipped throughout on both sides with equal lips.

*Cavity.*—Rounded with suture showing on one side. Depth $\frac{1}{4}''$, breadth $\frac{3}{8}''$. Base rounded; apex, short, truncate; pistil point, apical in form — a small, rounded hump with a depression on the side opposite the suture.

*Stem.*—Medium size $\frac{1}{2}''$ in length.

*Skin.*—Medium thickness, medium texture; tenacious to flesh. Only slight tendency to crack. Color: Resembling Wind (56 J-7).

*Bloom.*—Abundant (now shown in the drawing).

*Flesh.*—Color: Resembling Macaroon (12 H-7).

*Surfaxce of pit cavity.*—Color, greenish-yellow with numerous brown fibres.

*Amygdalin.*—Moderate.

*Texture.*—Firm, crisp.

*Fibres.*—Abundant, fine, tender.

*Ripens.*—Evenly.

*Flavor.*—Mild.

*Aroma.*—Wanting.

*Eating quality.*—Good.

STONE

Type: Clingstone.

Form: Oval; oblique base, cuneate toward apex.

Hilum: Narrow, round.

Apex: Acute with equal sides.

Surface: Rugose; fin on dorsal edge, groove on dorsal edge.

Ridges: None.

Color: Brown (13 H-12).

Pit wall: 1/16″ thick.

Tendency to split: Slight.

Kernel: Oval form, bitter taste, viable. $\frac{3}{8}''$ in width, $\frac{1}{2}''$ in length. Yellow pellicle. Abundant amygdalin.

USE

For local market, long distance shipping, Keeping and shipping quality good. No unusual susceptibilities to insects or disease.

I claim:

1. A new and distinct variety of clingstone plum tree substantially as illustrated and described, which most nearly resembles its parent plant El Dorado plum, a non-intra varietal pollinator, but is distinguished therefrom and an improvement thereon in that it is a more vigorous tree and bears fruit which ripens about three to five days earlier, is somewhat larger in size, and has a darker maroon skin color.

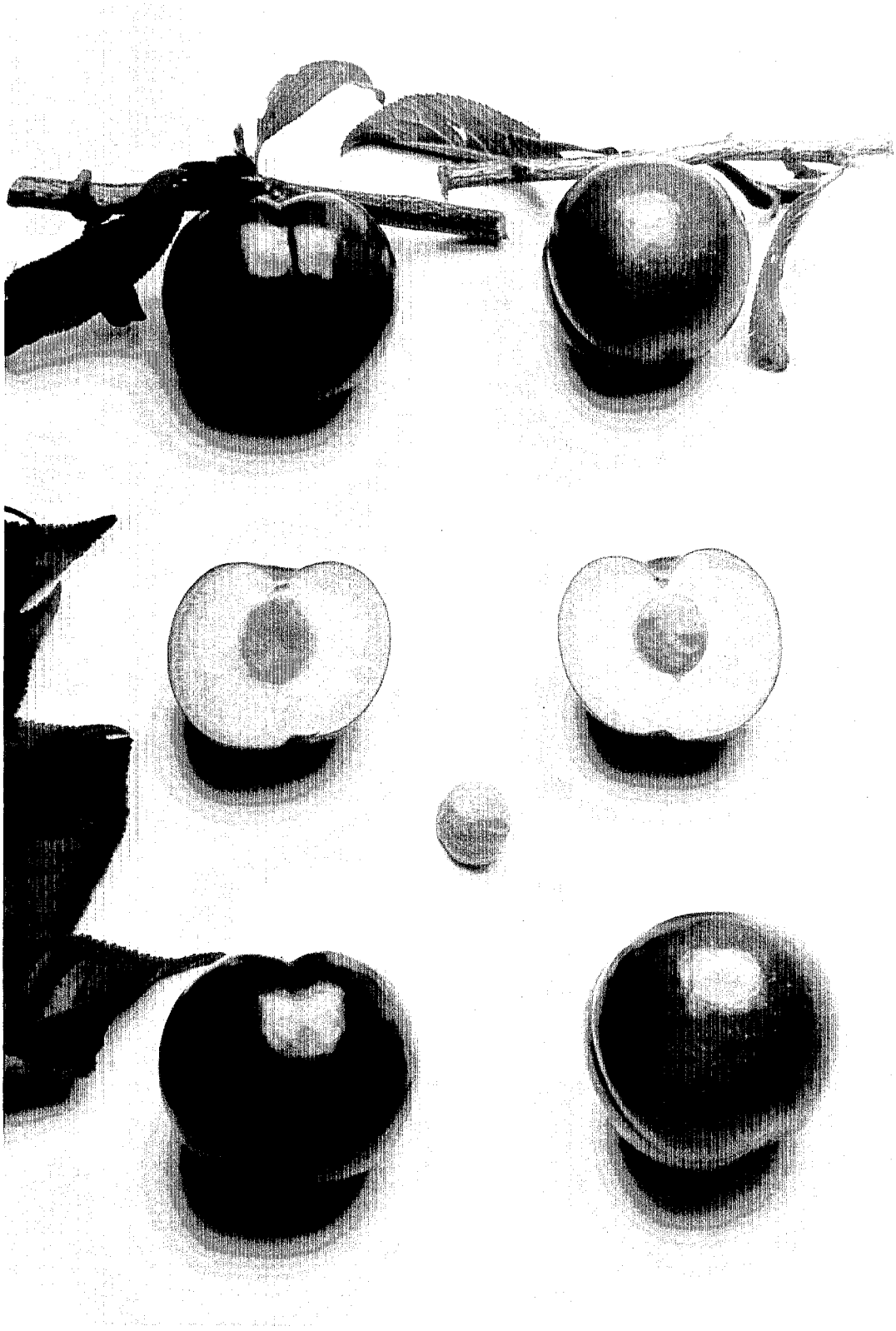

* * * * *